United States Patent
Wang et al.

(10) Patent No.: US 9,020,236 B2
(45) Date of Patent: Apr. 28, 2015

(54) METHOD FOR TOOTH SURFACE CLASSIFICATION

(75) Inventors: Wei Wang, Minhang (CN); Liwei Song, Pudong (CN); Yingqian Wu, Pudong (CN); Victor C. Wong, Rochester, NY (US); Jiayong Yan, Minhang (CN)

(73) Assignee: Carestream Health, Inc., Rochester, NY (US)

( * ) Notice: Subject to any disclaimer, the term of this patent is extended or adjusted under 35 U.S.C. 154(b) by 95 days.

(21) Appl. No.: 14/002,998

(22) PCT Filed: Mar. 19, 2012

(86) PCT No.: PCT/US2012/029646
§ 371 (c)(1),
(2), (4) Date: Oct. 24, 2013

(87) PCT Pub. No.: WO2012/129160
PCT Pub. Date: Sep. 27, 2012

(65) Prior Publication Data
US 2014/0037180 A1    Feb. 6, 2014

Related U.S. Application Data

(60) Provisional application No. 61/454,761, filed on Mar. 21, 2011.

(51) Int. Cl.
*G06K 9/00* (2006.01)
*G06T 7/00* (2006.01)
*A61B 5/00* (2006.01)
(Continued)

(52) U.S. Cl.
CPC ............ *G06T 7/0012* (2013.01); *A61B 5/0088* (2013.01); *A61B 6/14* (2013.01); *A61B 6/5217* (2013.01); *A61C 9/0046* (2013.01); *A61B 5/0071* (2013.01); *A61B 5/4547* (2013.01); *G01J 3/508* (2013.01); *G06K 2209/05* (2013.01); *G06T 2207/10064* (2013.01); *G06T 2207/20081* (2013.01); *G06T 2207/30036* (2013.01); *A61B 5/7267* (2013.01)

(58) Field of Classification Search
None
See application file for complete search history.

(56) References Cited

U.S. PATENT DOCUMENTS 8,897,902 B2 * 11/2014 See et al. ................. 700/56
2005/0244794 A1 11/2005 Kemp et al.
(Continued)

OTHER PUBLICATIONS

International Search Report completed Sep. 26, 2012 for International Application No. PCT/US2012/029646, 3 Pages.
(Continued)

*Primary Examiner* — Stephen R Koziol
*Assistant Examiner* — Amandeep Saini

(57) ABSTRACT

A method for intraoral imaging obtains a digital image of one or more teeth and detects first and second boundaries. At each of the first and second boundaries, there is calculated a boundary ratio of mean gray-scale values for the tooth area on one side of the boundary to mean gray-scale values for background areas on the other side. The calculated boundary ratios are stored. A third ratio of the mean gray-scale values for the tooth area near the first boundary to the mean gray-scale values for the tooth area near the second boundary is calculated and stored. A vector is formed and stored that contains at least the calculated boundary ratios and the third ratio. The tooth surface is classified as either smooth or occlusal according to the stored vector. The image data is processed according to the classification and processing results are reported.

10 Claims, 11 Drawing Sheets

(51) Int. Cl.
*A61B 6/14* (2006.01)
*A61B 6/00* (2006.01)
*A61C 9/00* (2006.01)
*G01J 3/50* (2006.01)

(56) References Cited

U.S. PATENT DOCUMENTS

2006/0223032 A1   10/2006   Fried
2008/0232662 A1    9/2008   Komiya
2009/0185712 A1    7/2009   Wong
2009/0322868 A1   12/2009   Ikeda
2010/0322490 A1   12/2010   Pan
2013/0243276 A1*   9/2013   Souza et al. .................. 382/128
2013/0308843 A1*  11/2013   Tank .............................. 382/128

OTHER PUBLICATIONS

European Search Report mailed Aug. 7, 2014 for European Patent Application No. 12 76 0500.4, 2 pages.

* cited by examiner

METHOD FOR TOOTH SURFACE CLASSIFICATION

CROSS REFERENCE TO RELATED APPLICATIONS

This application claims the benefit of and is a US national phase filing of PCT application No. PCT/US2012/029646 filed Mar. 19, 2012 that is entitled "A METHOD FOR TOOTH SURFACE CLASSIFICATION" in the names of Wei Wang, Liwei Song, Yingqian Wu, Victor C. Wong and Jiayong Yan; which itself claims benefit of Provisional application U.S. Ser. No. 61/454,761, provisionally filed on Mar. 21, 2011 that is entitled "A METHOD FOR TOOTH SURFACE CLASSIFICATION" in the names of Wei Wang, Liwei Song, Yingqian Wu, Victor C. Wong and Jiayong Yan; the disclosures of both priority applications are incorporated herein by reference in their entirety.

FIELD OF THE INVENTION

The invention relates generally to intraoral and dental imaging. More specifically, the invention relates to methods for classifying the tooth surface for subsequent processing.

BACKGROUND OF THE INVENTION

In spite of improvements in detection, treatment, and prevention techniques, dental caries remains a widely prevalent condition affecting people of all age groups. If not properly and promptly treated, caries can lead to permanent tooth damage and even to loss of teeth.

Traditional methods for caries detection include visual examination and tactile probing with a sharp dental explorer device, often assisted by radiographic (x-ray) imaging. Detection using these methods can be somewhat subjective, varying in accuracy due to many factors, including practitioner expertise, location of the infected site, extent of infection, viewing conditions, accuracy of x-ray equipment and processing, and other factors. There are also hazards associated with conventional detection techniques, including the risk of damaging weakened teeth and spreading infection with tactile methods as well as exposure to x-ray radiation. By the time caries is evident under visual and tactile examination, the disease is generally in an advanced stage, requiring a filling and, if not timely treated, possibly leading to tooth loss.

In response to the need for improved caries detection methods, there has been considerable interest in improved imaging techniques that do not employ x-rays. One method that has been commercialized employs fluorescence, caused when teeth are illuminated with high intensity blue light. This technique, termed quantitative light-induced fluorescence (QLF), operates on the principle that sound, healthy tooth enamel yields a higher intensity of fluorescence under excitation from some wavelengths than does de-mineralized enamel that has been damaged by caries infection. The strong correlation between mineral loss and loss of fluorescence for blue light excitation is then used to identify and assess carious areas of the tooth. A different relationship has been found for red light excitation, a region of the spectrum for which bacteria and bacterial by-products in carious regions absorb and fluoresce more pronouncedly than do healthy areas.

It is recognized that, with fluorescence techniques, the image contrast that is obtained corresponds to the severity of the condition. Accurate identification of caries using these techniques often requires that the condition be at a more advanced stage, beyond incipient or early caries, because the difference in fluorescence between carious and sound tooth structure is very small for caries at an early stage. In such cases, detection accuracy using fluorescence techniques may not show marked improvement over conventional methods. Because of this, the use of fluorescence effects appears to have some practical limits that prevent accurate diagnosis of incipient caries. As a result, a caries condition may continue undetected until it is more serious, requiring a filling, for example.

Detection of caries at very early stages is of particular interest for preventive dentistry. As noted earlier, conventional techniques generally fail to detect caries at a stage at which the condition can be reversed. As a general rule of thumb, incipient caries is a lesion that has not penetrated substantially into the tooth enamel. Where such a caries lesion is identified before it threatens the dentin portion of the tooth, remineralization can often be accomplished, reversing the early damage and preventing the need for a filling. More advanced caries, however, grows increasingly more difficult to treat, most often requiring some type of filling or other type of intervention.

In order to take advantage of opportunities for non-invasive dental techniques to forestall caries, it is desirable that caries be detected at the onset. In many cases, this level of detection has been found to be difficult to achieve using existing fluorescence imaging techniques, such as QLF. As a result, early caries can continue undetected, so that by the time positive detection is obtained, the opportunity for reversal using low-cost preventive measures can be lost.

In commonly-assigned U.S. Patent Application Publication No. 2008/0056551, a method and apparatus that employs both the reflectance and fluorescence images of the tooth is used to detect caries. It employs observed back-scattering, or reflectance, for incipient caries and in combination with fluorescence effects, to provide an improved dental imaging technique to detect caries. The technique, referred to as Fluorescence Imaging with Reflectance Enhancement (FIRE), promotes the contrast of images over that of earlier approaches, and to detect incipient caries at stages when preventive measures are likely to take effect. Advantageously, FIRE detection can be accurate at an earlier stage of caries infection than has been exhibited using existing fluorescence approaches that measure fluorescence alone. The application describes a downshifting method to generate the FIRE image.

Commonly-assigned copending PCT/CN2009/000078, entitled METHOD FOR DETECTION OF CARIES describes a morphological method for generating a FIRE image with reduced sensitivity to illumination variation.

The tooth surface itself is complex. Buccal and lingual surfaces of the tooth are characteristically smooth, with a contour that changes gradually from one side of the tooth to the other. Occlusal surfaces, on the other hand, are typically pitted and have significant number of transitions in slope and contour over the tooth surface. As a result of these differences in surface characteristics, the same types of image processing and analysis techniques often do not work equally well with both types of tooth surface. The characteristic appearance of caries areas along buccal or lingual surfaces can differ in significant ways from caries occlusal surfaces. These dissimilar types of surfaces can respond differently with respect to contrast of caries regions and specular reflection, for example. Hypo-mineralization and other effects can confuse image processing algorithms designed to detect suspicious caries areas.

In addition to caries detection, characterization of the tooth surface can also be useful for other types of intraoral and dental image processing, including processing that relates to tooth shade and appearance, for example, and for overall classification of intraoral images.

Thus, it can be seen that it would be helpful to classify tooth surface type before attempting to apply caries detection techniques as well as for other processing. This added step in image analysis can help to improve the accuracy of caries detection and reduce the number of false positives.

SUMMARY OF THE INVENTION

An object of the present invention is to advance the art of image processing for detection of dental caries. Embodiments of the present invention address the need to classify tooth surfaces more accurately so that appropriate image processing methods can be used, depending on the nature of the tooth surface. An advantage of the method of the present invention is that it can automatically determine whether a tooth surface is smooth or occlusal, without operator intervention, thereby reducing the number of false positives when caries detection algorithms are subsequently applied.

Accordingly, there is described a tooth surface classification method with one or more of the following advantages: (1) the tooth surface can be classified automatically; (2) results are relatively robust and insensitive to illumination variation; (3) the method does not utilize extensive calculation complexity and can be executed real-time; (4) the method can be used for caries detection in a still image or in a video image, with auto-highlighting. This method can be readily used with a number of different types of intra oral camera imaging systems. Applying this method can help to reduce the amount of time needed to properly assess the condition of a patient's teeth.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for intraoral imaging, the method executed at least in part on a computer system and comprising: obtaining a digital image of one or more teeth; detecting first and second boundaries of the one or more teeth; calculating, at each of the first and second boundaries, a boundary ratio of mean gray-scale values for the tooth area on one side of the boundary to mean gray-scale values for background areas on the other side of the boundary and storing the calculated boundary ratios in a memory; calculating a third ratio of the mean gray-scale values for the tooth area near the first boundary to the mean gray-scale values for the tooth area near the second boundary and storing the third ratio in the memory; forming and storing a vector that contains at least the calculated boundary ratios and the third ratio; classifying a tooth surface as either smooth or occlusal according to the stored vector; processing the digital image according to the tooth surface classification; and reporting the processing results.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
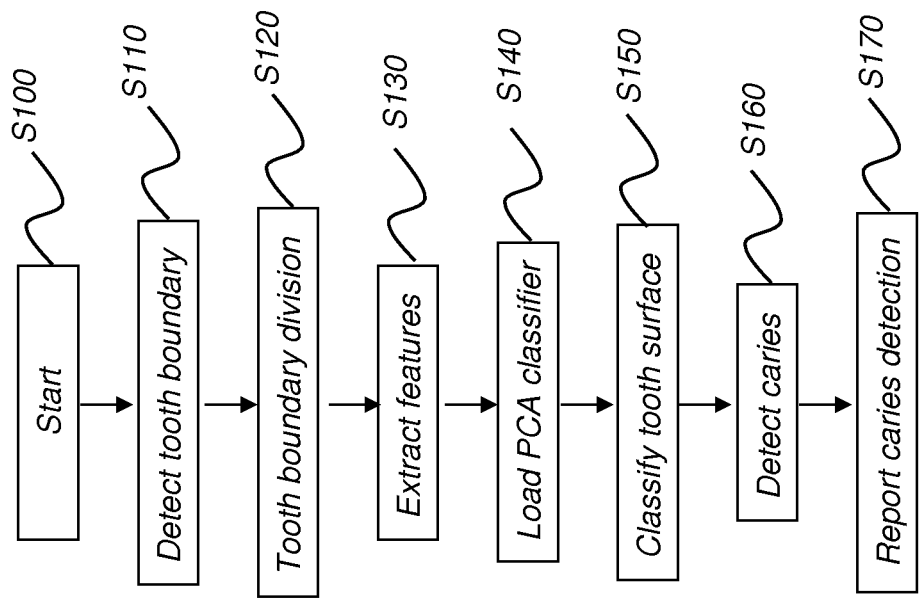
FIG. 1 is a logic flow diagram that shows steps for caries detection.

The following is a detailed description of the preferred embodiments of the invention, reference being made to the drawings in which the same reference numerals identify the same elements of structure in each of the several figures.

This application claims priority to U.S. Provisional Application No. 61/454,761 filed on Mar. 21, 2011 entitled, "A METHOD FOR TOOTH SURFACE CLASSIFICATION", incorporated herein in its entirety by reference.

Where they are used, the terms "first", "second", "third", and so on, do not necessarily denote any ordinal or priority relation, but may be used for more clearly distinguishing one element or time interval from another.

The term "highlighting" for a displayed feature has its conventional meaning as is understood to those skilled in the information and image display arts. In general, highlighting uses some form of localized display enhancement to attract the attention of the viewer. Highlighting a portion of an image, such as an individual tooth or other structure, or a path from one feature to the next, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

Figure 3:
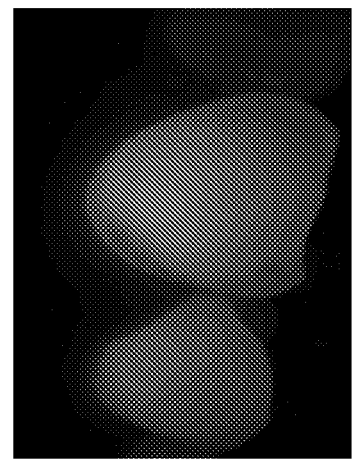
FIG. 3 is an exemplary fluorescence image of teeth.
Figure 2:
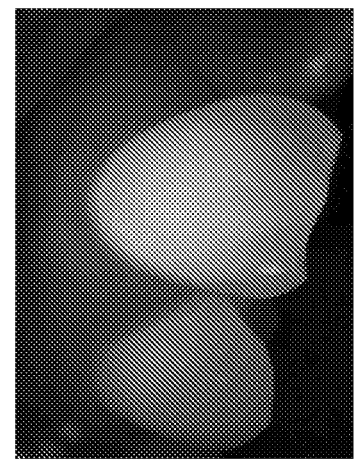
FIG. 2 is an exemplary white light image of teeth.

The logic flow diagram of FIG. 1 shows steps in a sequence for caries detection according to an embodiment of the present invention. In an initialization step S100, digital image data for one or more teeth is obtained for analysis. A boundary detection step S110 is executed, calculating the tooth boundary based on the result of tooth region segmentation. An image normalization step is executed to normalize the pixel intensity values to a preset range that is suitable for subsequent image processing. By way of example, FIG. 2 shows a normalized white light image 10. FIG. 3 shows a corresponding fluorescence image 20.

Background area detection then follows, in which tooth region segmentation utilities are employed to separate the tooth areas from gum and background areas. Because the intensities in tooth and gum areas may be higher than that of the background, the background areas can initially be detected based on threshold techniques. In the current algorithm, a fixed threshold value is used to process the normalized white light image. Alternately, corresponding channels of the white light image and the fluorescence image 20 of FIG. 3 are used for thresholding. In this alternate sequence, the algorithm thresholds the green channel of the white light image and the fluorescence image, respectively. Then, the union of these threshold regions is computed, in which the threshold results from the white light image and fluorescence image are taken as the background areas.

Continuing with the sequence of FIG. 1, gum areas are detected as part of boundary detection step S110. Because the gum is red in the white light image, it can be readily identified and removed with the color information. According to an embodiment of the present invention, the ratio between red and green channels of white light image is used to distinguish gum from tooth areas. If the ratio of color channels within a certain region is higher than a preset value, the corresponding portion of the image is calculated as a gum area. After the background and gum areas are removed, the regions that remain are considered as part of the tooth region.

Figure 5:
FIG. 5 shows thresholding to identify gum tissue content.
Figure 4:
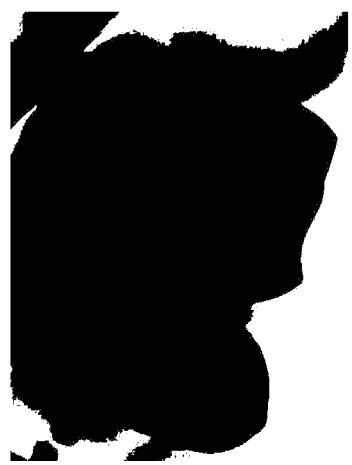
FIG. 4 shows thresholding to identify background content.
Figure 7:
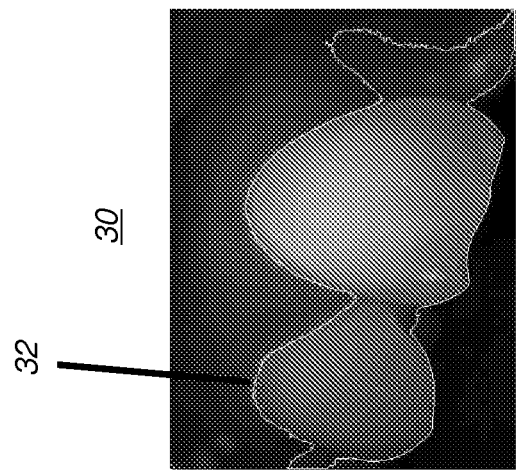
FIG. 7 is an image showing boundary division for the teeth of FIGS. 1 and 2.
Figure 6:
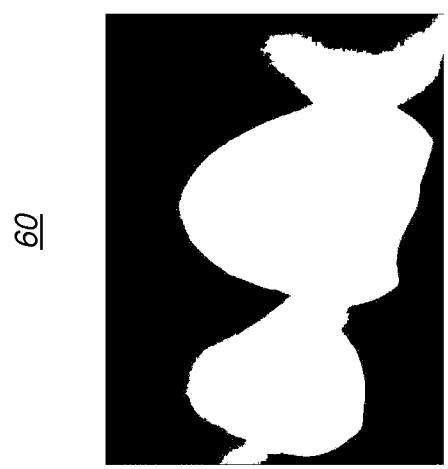
FIG. 6 shows thresholding to identify tooth content.

FIGS. 4-6 show example binary threshold images that are used to provide segmentation results for the images shown in FIGS. 2-3. FIG. 4 shows a background area image 40, with image content that is neither tooth nor gum tissue shown in white. FIG. 5 shows a gum area image 50, with the gum tissue shown in white. FIG. 6 shows a tooth area image 60, with tooth content shown in white. As shown in FIG. 7, an outline 32 can be traced along the border of the tooth region, thereby identifying the tooth boundary for display in a boundary image 30, for example.

Figure 8:
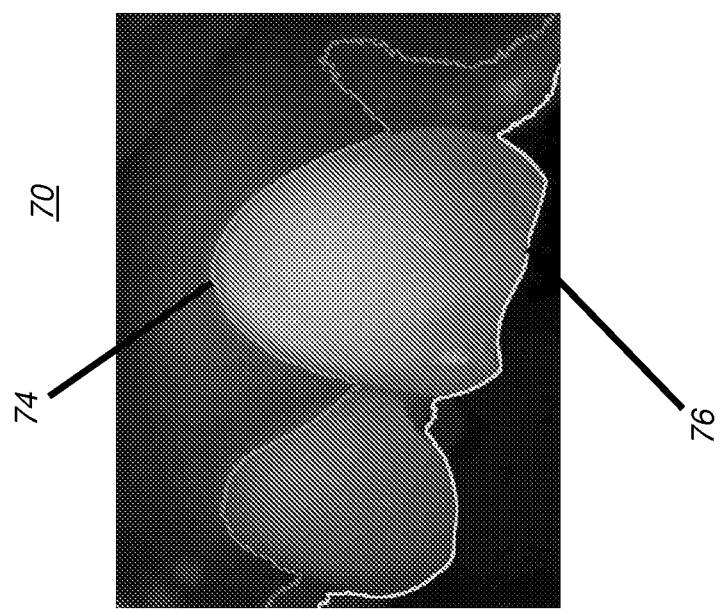
FIG. 8 is an image that shows boundary division for a buccal view.

After the tooth boundary is detected, the tooth boundary is divided into two sections in a boundary division step S120 (FIG. 1) according to location information. Then the features can be extracted based on the divided tooth boundary. For buccal and lingual surfaces, the tooth boundary separation identifies two sections, a first section near the gum areas and a second section near background areas. FIG. 8 shows a boundary division image 70 for a buccal surface. Boundary lines 74 and 76 indicate the different boundary sections for this surface type. Non-tooth areas that border line 74 are gum areas, having higher pixel intensity values in the green channel. Non-tooth areas that border line 76 are background areas, having lower pixel intensity values in the green channel.

Figure 9:
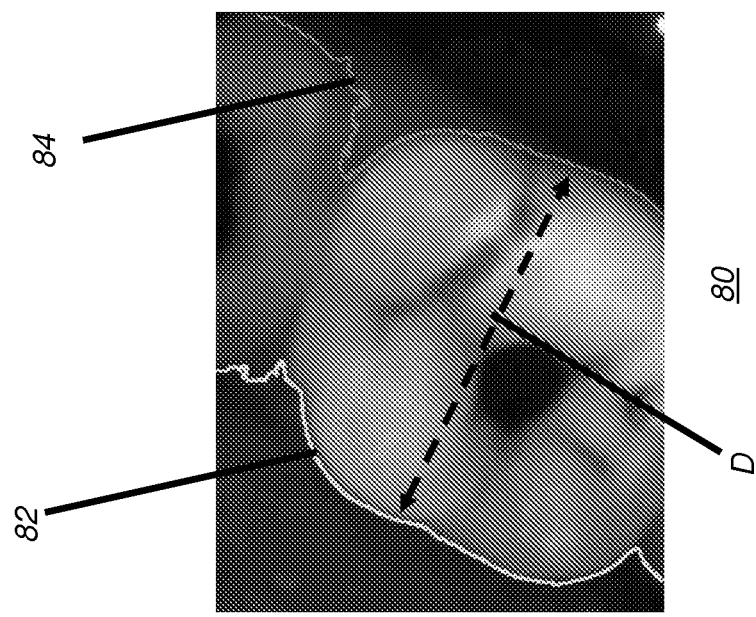
FIG. 9 is an image that shows boundary division for an occlusal view.

For an occlusal surface, as shown in image 80 in FIG. 9, the tooth boundary is divided into two sections following the direction of the tooth array. One section is indicated by a line 82; non-tooth areas neighboring this line have lower pixel intensity values in the green channel. The other section is highlighted by a line 84; non-tooth areas neighboring this line have higher pixel intensity values in the green channel. Boundaries are separated by a distance D that can vary across the tooth and along the image.

Figure 10:
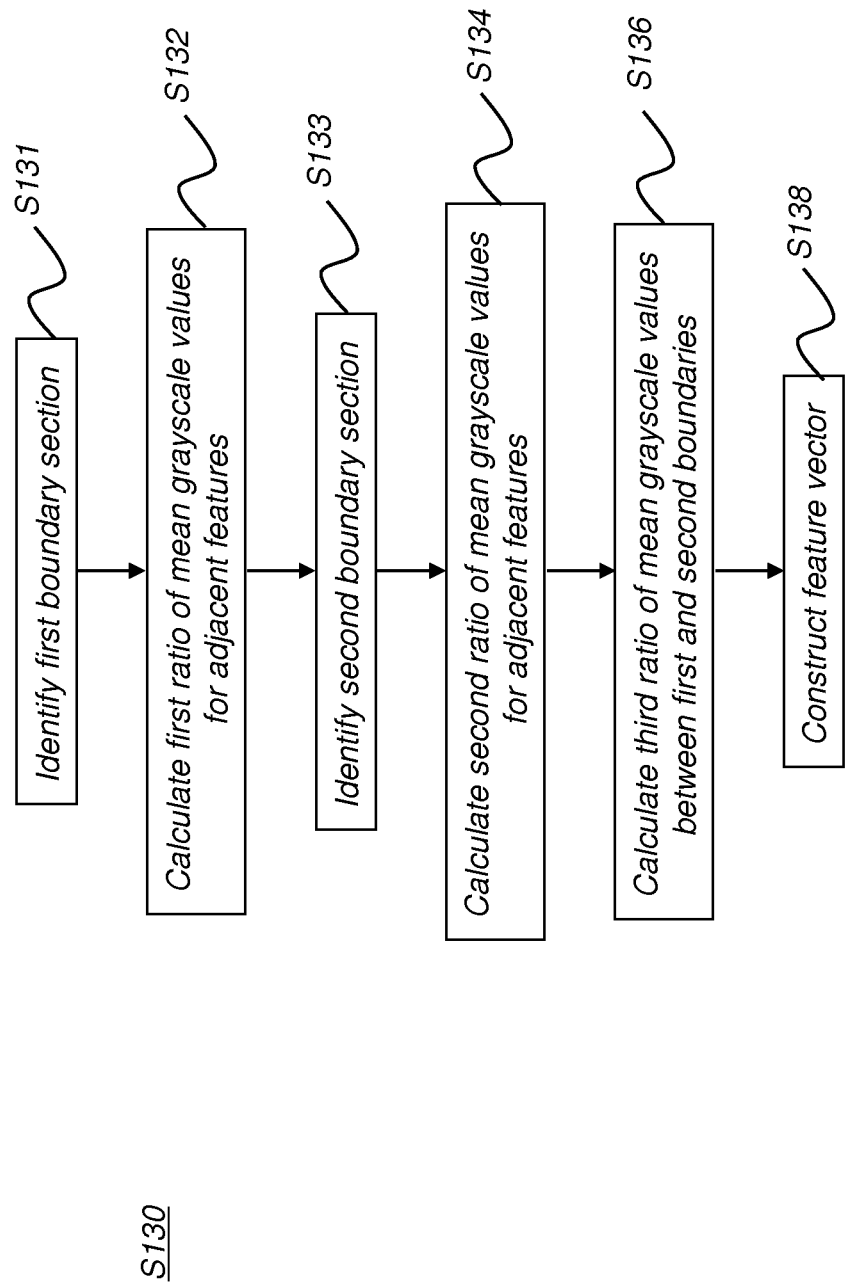
FIG. 10 is a logic flow diagram that shows processing steps for constructing a feature vector used for tooth classification.
Figure 11A:
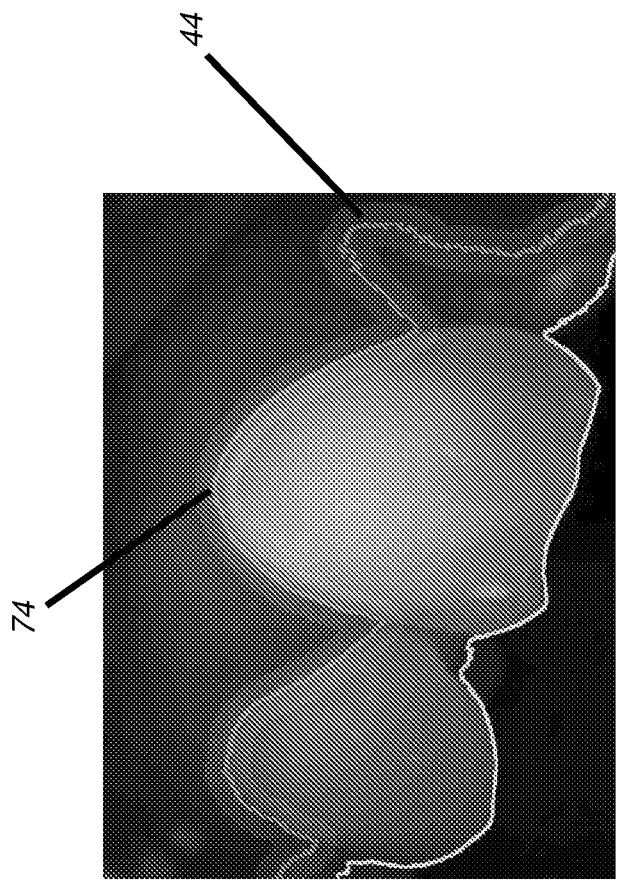
FIG. 11A is an image that shows dilation of a boundary line for subsequent grayscale ratio computation.

Referring again to the sequence of FIG. 1, a feature extraction step S130 then uses the results of boundary division step S120 for further classification of the tooth surface. The logic flow diagram of FIG. 10 shows a sequence of steps used in feature extraction step S130. An identification step S131 identifies a first boundary section from boundary division step S120, such as the boundary identified along the gum line by line 74 in FIG. 8, for example. Referring to FIG. 11A, this first boundary curve is initially expanded using morphological imaging techniques, such as image dilation, for example. This expands line 74 and defines a first boundary section 44.

Figure 11C:
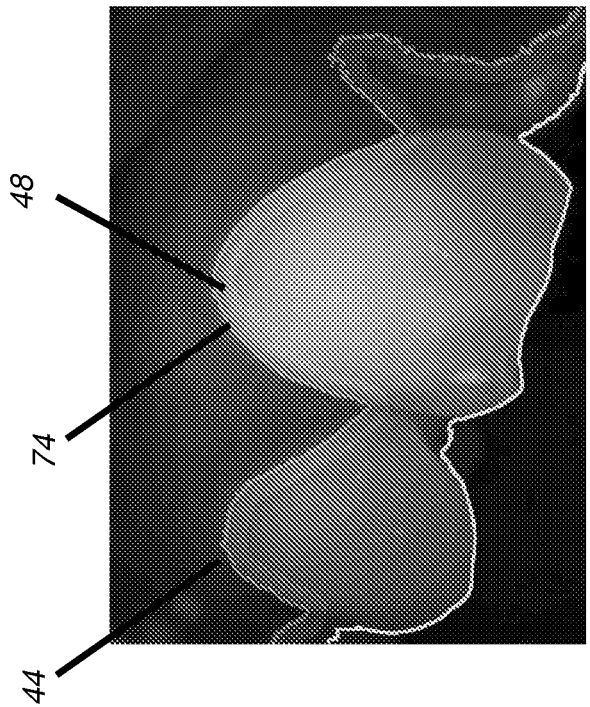
FIG. 11C is an image that shows identifying a region on the other side of the boundary line for mean grayscale computation.
Figure 11B:
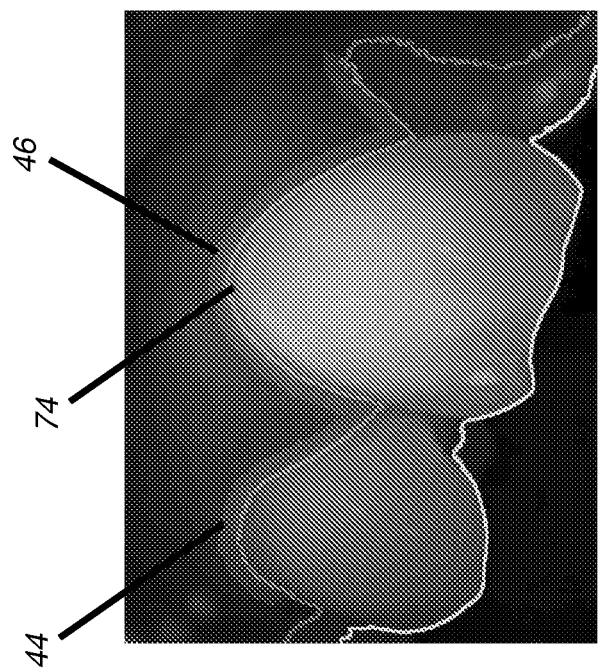
FIG. 11B is an image that shows identifying a region on one side of the boundary line for mean grayscale computation.

Continuing with the FIG. 10 sequence, subsequent substeps divide first boundary section 44 into two parts, as shown in FIGS. 11B and 11C. FIG. 11B shows how a first part 46 is defined as that portion of first boundary section 44 that lies to, or overlaps, the gum tissue side of line 74. This portion has a gray-scale distribution value FeaUpperGum, computed as the mean value or other statistical value in the neighboring gum areas.

FIG. 11C shows how a second part 48 is defined as that portion of first boundary section 44 that overlaps the tooth side of line 74. This portion has a gray-scale distribution value FeaUpperTooth, computed as the mean value or other statistical value in the neighboring tooth areas.

Given these defined regions, a first ratio calculation step S132 then calculates and stores in a memory a value Feature1 that is computed as the first boundary ratio of mean gray-scale values for the tooth area near one side of the boundary, second part 48, to the mean gray-scale value for gum areas near the other side of the boundary, first part 46, that is:

Feature1=FeaUpperTooth/FeaUpperGum or, alternately, the ratio expressed as its inverse:

Feature1b=FeaUpperGum/FeaUpperTooth

In the context of the present disclosure, the term "near" at a particular location means within one-third of the total distance between boundaries, preferably closer than one-third of this length. FIG. 9 shows a typical distance D between boundaries.

Figure 12A:
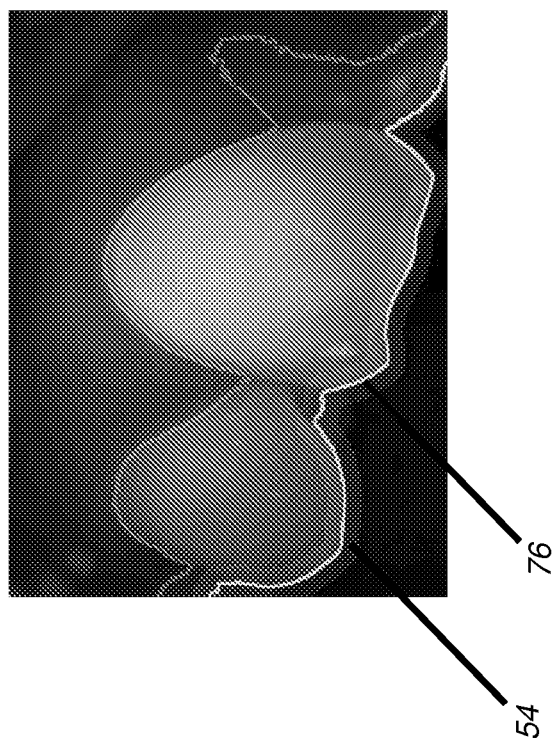
FIG. 12A is an image that shows dilation of a boundary line for subsequent grayscale ratio computation.
Figure 12C:
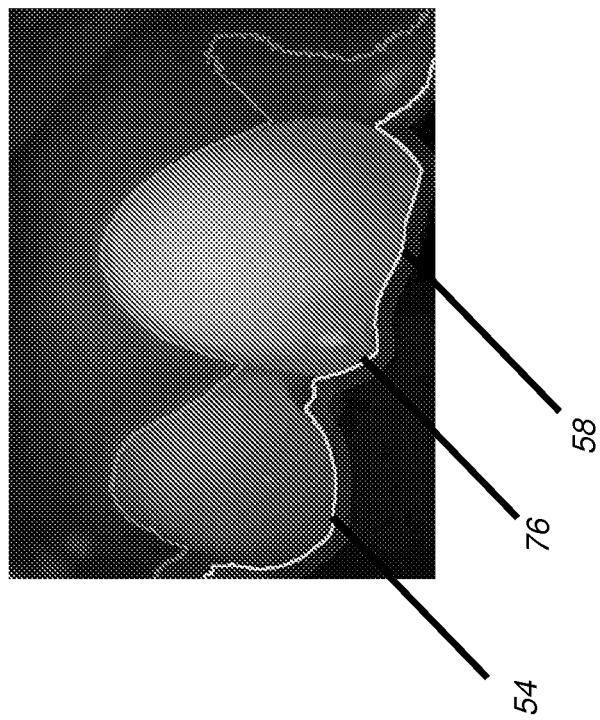
FIG. 12C is an image that shows identifying a region on the other side of the boundary line for mean grayscale computation.
Figure 12B:
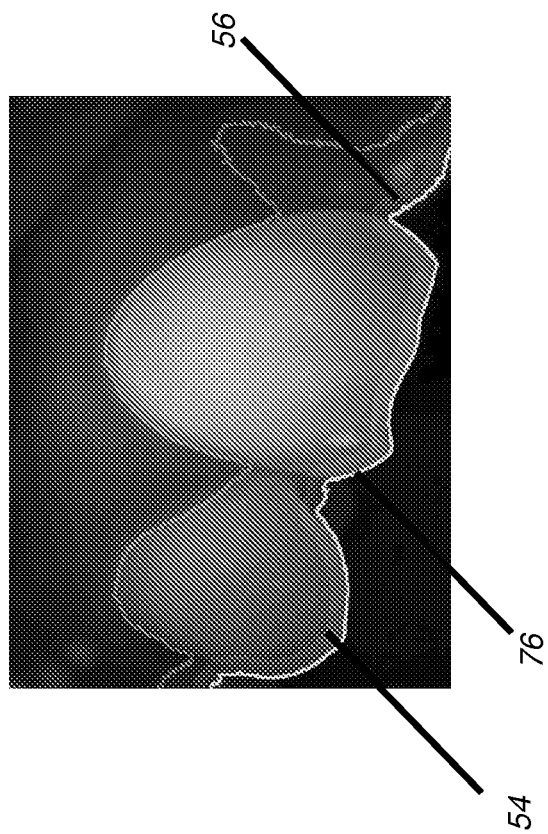
FIG. 12B is an image that shows identifying a region on one side of the boundary line for mean grayscale computation.

Continuing with the FIG. 10 sequence, a subsequent identification step S133 identifies a second boundary section from boundary division step S120, such as the boundary identified along the background by line 76 in FIG. 8, for example. Referring to FIG. 12A, this second boundary curve is initially expanded using morphological imaging techniques, such as image dilation, for example. This expands line 76 and defines a second boundary section 54. A second ratio calculation step S134 then calculates and stores in memory a second boundary ratio of mean gray-scale values for the tooth area near one side of the boundary to the mean gray-scale value for background areas near the other side of the boundary. FIGS. 12A, 12B, and 12C illustrate how the individual areas are identified, similar to the sequence shown in FIGS. 11A, 11B, and 11C.

Continuing with the FIG. 10 sequence, subsequent substeps divide second boundary section 54 into two parts, as shown in FIGS. 12B and 12C. FIG. 12B shows how a first part 56 is defined as that portion of second boundary section 54 that lies to, or overlaps, the tooth tissue side of line 76. This portion has a gray-scale distribution value FeaLowerTooth, computed as the mean value or other statistical value in the neighboring tooth areas.

FIG. 12C shows how a second part 58 is defined as that portion of second boundary section 54 that overlaps the background side of line 76. This portion has a gray-scale distribution value FeaLowerBack, computed as the mean value or other statistical value in the neighboring background areas.

Given these defined regions, a second ratio calculation step S134 then calculates and stores in a memory a value Feature2 that is computed as:

Feature2=FeaLowerTooth/FeaLowerBack or, alternately, the ratio expressed as its inverse:

Feature2b=FeaLowerBack/FeaLowerTooth

A third ratio calculation step S136 in FIG. 10 then calculates and stores the ratio of mean gray-scale values for tooth areas near the first and second boundary sections. That is:

Feature3=FeaUpperTooth/FeaLowerTooth or, alternately, its inverse:

Feature3b=FeaLowerTooth/FeaUpperTooth

A three-dimensional feature vector or similar data structure is then formed using the calculated ratio data from preceding steps in a feature vector generation step S138. The generated vector thus includes the first boundary ratio, the second boundary ratio, and the third ratio. The feature vector that is formed in this way can then be stored and used for tooth surface classification.

Three-dimensional vector construction can use Feature1, Feature2, and Feature3, or their inverses, in any suitable order. Alternately, a two-dimensional vector can be formed using [Feature1, Feature2] or [Feature2, Feature1]

An optional vector normalization process generates a normalized feature vector, such as:

$$FeatureNorm = \left[ \frac{Feature1 - \mu_1}{\sigma_1} \quad \frac{Feature2 - \mu_2}{\sigma_2} \quad \frac{Feature3 - \mu_3}{\sigma_3} \right]$$

wherein values $\mu_1$-$\mu_3$ correspond to preset values, i.e. the mean value of Feature1~Feature3 calculated from a training data set. Similarly, values $\sigma_1$-$\sigma_3$ correspond to the preset values, i.e. the variance of Feature1~Feature3 calculated from the training data set. The normalization process is similar for a two-dimensional feature vector. The feature vector can then serve as input to the classification process.

A classifier loading step S140 (FIG. 1) loads an appropriate classifier for tooth surface classification. According to one embodiment of the present invention, classifier loading step S140 loads a PCA (principal component analysis) classifier for this task. Principal component analysis (PCA) is a mathematical technique that uses an orthogonal transformation to convert a set of observations of possibly correlated variables into a set of values of linearly uncorrelated variables called principal components. The number of principal components is less than or equal to the number of original variables. A PCA classifier is typically developed using neural-network techniques that allow the classifier software to be trained using a test sample set. While PCA classification tools are particularly well-suited for shape and contour classification, other classifier types could alternately be used. Once the classifier is sufficiently trained to distinguish surface characteristics, it can then be stored for use in analyzing patient images in a classification step S150. Classification then defines the tooth image as either a buccal or lingual surface or an occlusal surface image.

Figure 13:
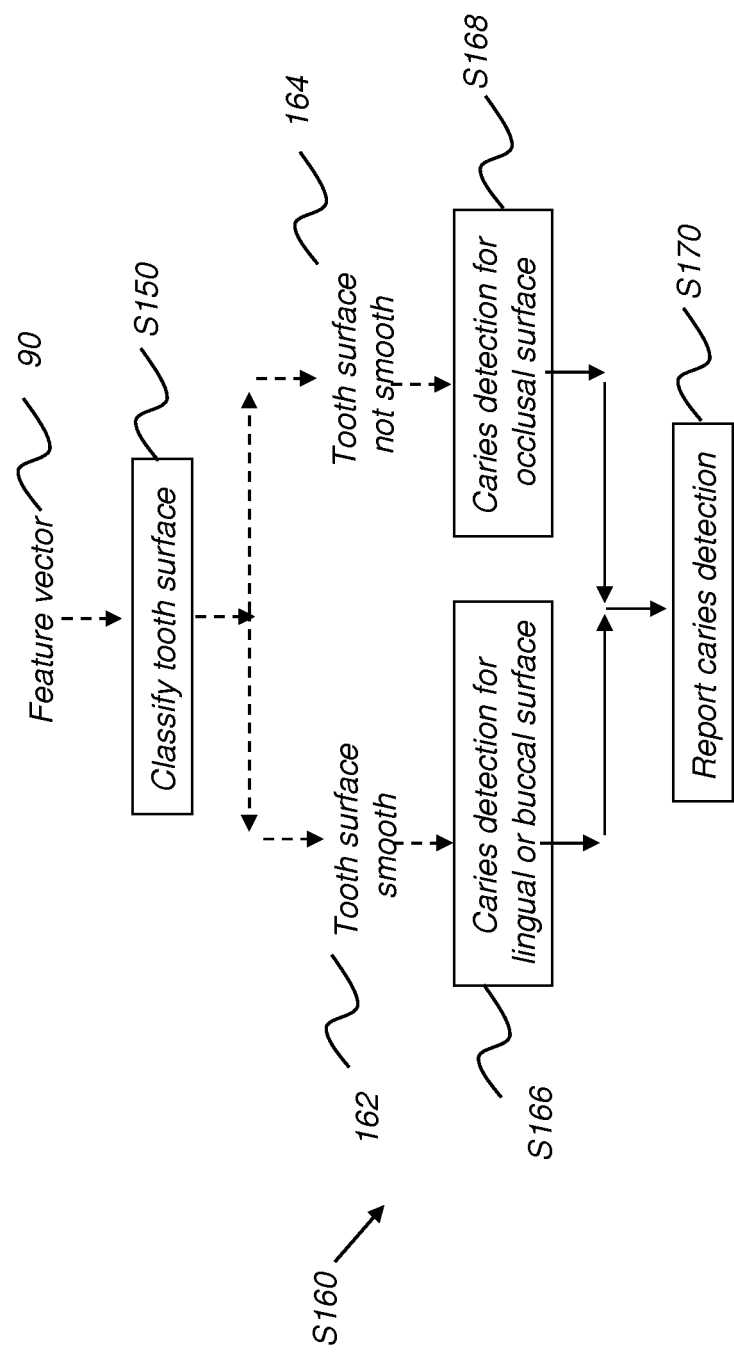
FIG. 13 is a logic flow diagram that expands upon the detection step of FIG. 1.

Still following the sequence of procedures in FIG. 1 and using the expanded logic flow shown in FIG. 13, after a feature vector 90 is processed in classification step S150, a caries detection step S160 is then executed once classification has been completed. As shown in the logic flow of FIG. 13, caries detection step S160 applies different parameters or algorithms, depending on the type of surface classification that has been identified. Where results 162 indicate a smooth surface, a caries detection step S166 is applied for lingual or surfaces. When results 164 indicate a rough surface, a caries detection step S168 is applied for occlusal surfaces. A reporting step S170 then reports on the results of caries detection, such as by listing the tooth number and surface or highlighting one or more caries sites on a display console that shows the imaged tooth, for example. It should be noted that caries detection step S160 is one type of image processing that can use the tooth surface classification provided in the sequence shown in FIG. 1. Alternate processing steps could be provided to use the tooth surface classification in other ways, such as for analyzing tooth appearance or for classifying image views, for example.

As will be appreciated by one skilled in the art, the present invention may be embodied as a system or method, with parts of the system executed using a computer program product or other control logic processor device that is programmed with instructions for obtaining and displaying an image, accepting operator instructions and input data, and responding to the operator entries. Accordingly, an embodiment of the present invention may be in the form of an entirely hardware embodiment or an embodiment combining software and hardware aspects that may all generally be referred to herein as a "circuit" or "system." Furthermore, parts of the present invention may take the form of a computer program product embodied in a computer-readable storage medium, with instructions executed by one or more computers or host processors. This medium may comprise, for example: magnetic storage media such as a magnetic disk (such as a hard drive or storage disk) or magnetic tape; optical storage media such as an optical disc, optical tape, or machine readable bar code; solid state electronic storage devices such as solid state hard drives, random access memory (RAM), or read only memory (ROM); or any other physical device or medium employed to store a computer program. The computer program for performing the method of the present invention may also be stored on computer readable storage medium that is connected to a host processor by way of the internet or other communication medium.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

Those skilled in the art will readily recognize that the equivalent of such a computer program product may also be constructed in hardware. The computer-usable or computer-readable medium could even be paper or another suitable medium upon which executable instructions are printed, as the instructions can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport computer instructions for use by, or in connection with, an instruction execution system, apparatus, or device.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations, such feature can be combined with one or more other features of the other implementations as can be desired and advantageous for any given or particular function.

The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal.

The invention claimed is:

1. A method for intraoral imaging, the method executed at least in part on a computer system and comprising:
   obtaining a digital image of one or more teeth;
   detecting first and second boundaries of the one or more teeth;
   calculating, at each of the first and second boundaries, a boundary ratio of mean gray-scale values for the tooth area on one side of the boundary to mean gray-scale values for background areas on the other side of the boundary and storing the calculated boundary ratios in a memory;
   calculating a third ratio of the mean gray-scale values for the tooth area near the first boundary to the mean gray-scale values for the tooth area near the second boundary and storing the third ratio in the memory;
   forming and storing a vector that contains at least the calculated boundary ratios and the third ratio;
   classifying a tooth surface as either smooth or occlusal according to the stored vector;
   processing the digital image according to the tooth surface classification; and
   reporting the processing results.

2. The method of claim 1 wherein the mean gray scale values are from portions of the image that are within one third of the distance between the first and second boundaries.

3. The method of claim 1 wherein classifying the tooth surface comprises using a principal component analysis classifier.

4. The method of claim 1 wherein classifying the tooth surface comprises using a trained classifier.

5. The method of claim 1 wherein processing the digital image according to the tooth surface classification comprises detecting one or more caries sites.

6. The method of claim 5 wherein reporting the processing results comprises highlighting the one or more caries site on a display.

7. The method of claim 1 wherein the stored vector is normalized according to values from a training data set.

8. The method of claim 1 wherein the boundaries include one or more of gum areas and background areas.

9. A method for caries detection, the method executed at least in part on a computer system that has a display and comprising:
   obtaining a digital image of one or more teeth;
   detecting first and second boundaries of the one or more teeth;
   calculating, at each of the first and second boundaries, a boundary ratio of mean gray-scale values for the tooth area on one side of the boundary to mean gray-scale values for background areas on the other side of the boundary and storing the calculated boundary ratios in a memory;
   calculating a third ratio of the mean gray-scale values for the tooth area near the first boundary to the mean gray-scale values for the tooth area near the second boundary and storing the third ratio in the memory;
   forming and storing a vector that contains at least the calculated boundary ratios and the third ratio;
   classifying a tooth surface as either smooth or occlusal according to the stored vector;
   processing the digital image to detect caries according to the tooth surface classification; and
   reporting the processing results on a display.

10. The method of claim 9 wherein reporting the processing results comprises highlighting one or more caries site on the display.

* * * * *